US009297820B2

(12) United States Patent
Iizumi et al.

(10) Patent No.: US 9,297,820 B2
(45) Date of Patent: Mar. 29, 2016

(54) AUTOMATIC ANALYZER

(75) Inventors: Noriko Iizumi, Hitachinaka (JP);
Tomoko Tomiyama, Hitachinaka (JP);
Yoshimitsu Takagi, Hitachinaka (JP);
Kyoko Imai, Hitachinaka (JP);
Ryuichiro Kodama, Hitachinaka (JP);
Tomonori Mimura, Kasama (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 392 days.

(21) Appl. No.: 12/369,187

(22) Filed: Feb. 11, 2009

(65) Prior Publication Data
US 2009/0202390 A1  Aug. 13, 2009

(30) Foreign Application Priority Data

Feb. 13, 2008 (JP) ................. 2008-031504

(51) Int. Cl.
*G01N 35/00* (2006.01)
(52) U.S. Cl.
CPC .... *G01N 35/00732* (2013.01); *G01N 35/00603* (2013.01); *G01N 35/00693* (2013.01); *G01N 2035/00821* (2013.01); *G01N 2035/00891* (2013.01)
(58) Field of Classification Search
None
See application file for complete search history.

(56) References Cited

U.S. PATENT DOCUMENTS

| | | | | |
|---|---|---|---|---|
| 5,314,825 A | * | 5/1994 | Weyrauch et al. | 436/43 |
| 5,325,295 A | * | 6/1994 | Fratantoni et al. | 356/427 |
| 5,730,939 A | * | 3/1998 | Kurumada et al. | 422/67 |
| 5,885,529 A | * | 3/1999 | Babson et al. | 422/65 |
| 6,090,630 A | * | 7/2000 | Koakutsu et al. | 436/50 |
| 6,440,369 B1 | * | 8/2002 | Oonuma et al. | 422/64 |
| 6,579,717 B1 | | 6/2003 | Matsubara et al. | |
| 6,708,121 B2 | * | 3/2004 | Arake et al. | 702/31 |
| 6,733,728 B1 | * | 5/2004 | Mimura et al. | 422/65 |
| 6,846,457 B1 | * | 1/2005 | Tokiwa et al. | 422/67 |
| 7,275,807 B2 | * | 10/2007 | Van Tuyl | 347/46 |
| 2004/0102997 A1 | * | 5/2004 | Kikuchi et al. | 705/1 |

(Continued)

FOREIGN PATENT DOCUMENTS

| | | |
|---|---|---|
| EP | 0 973 115 A2 | 1/2000 |
| EP | 1 835 291 A2 | 9/2007 |

(Continued)

OTHER PUBLICATIONS

European Search Report received in European Application No. 09001892.0 dated Nov. 14, 2013.

*Primary Examiner* — Jill Warden
*Assistant Examiner* — Benjamin Whatley
(74) *Attorney, Agent, or Firm* — Mattingly & Malur, PC

(57) ABSTRACT

An automatic analyzer includes a storage unit for storing operation information information about usage histories of expendable supplies provided for the analysis, and an analysis-ID control unit giving an ID to the analysis, the analysis ID being used as information for identifying the analysis to derive a calibration curve. Data stored in the storage unit is organized along the same time axis both in the order of samples subjected to the analysis and inspection, and in the order of analysis items, so that the data is output in a total data display area. The data is organized from the viewpoint of an analysis process of an analysis item of each sample. By use of information used to identify an influence range based on a kind of an abnormal state, which is stored beforehand, a judgment is made as to whether or not it is necessary to perform reinspection.

18 Claims, 11 Drawing Sheets

| ANALYSIS ID | SAMPLE No. | ANALYSIS ITEM | CELL No. | 1 | ... | 6 | 7 | 8 | 9 | ... | 21 |
|---|---|---|---|---|---|---|---|---|---|---|---|
| NOR210001 | N006242 | FE | 352 | S PIPETTING P1 | | R1 PIPETTING Pos. 1-2 | | R1M IX P2 | | | MEASUREMENT |
| NOR210002 | N006243 | FE | 36 | | | S PIPETTING P2 | R1 PIPETTING Pos. 1-2 | | R1M IX P2 | | |
| NOR210003 | N006244 | GOT | 126 | | | | | S PIPETTING P2 | R1 PIPETTING Pos. 2-7 | | |
| NOR210004 | N006245 | FE | 216 | | | | | | | | |
| CAL110121 | C123 | FE | 306 | | | | | | | | |
| NOR210005 | N006247 | ALT | 396 | | | | | | | | |
| NOR210006 | N006248 | FE | 80 | | | | | | | | S PIPETTING P1 |
| NOR210007 | N006249 | FE | 170 | | | | | | | | |

ALARM (PHOTOMETER IS ABNORMAL)! ~501

(56) References Cited

U.S. PATENT DOCUMENTS

| | | | |
|---|---|---|---|
| 2004/0224351 A1* | 11/2004 | Shinohara | 435/6 |
| 2005/0233325 A1* | 10/2005 | Kureshy et al. | 435/6 |
| 2006/0004530 A1* | 1/2006 | Miyamoto et al. | 702/30 |
| 2006/0153737 A1* | 7/2006 | Saito et al. | 422/68.1 |
| 2006/0210435 A1* | 9/2006 | Alavie et al. | 422/65 |
| 2007/0053793 A1* | 3/2007 | Maeda et al. | 422/63 |
| 2007/0212261 A1* | 9/2007 | Tanaka et al. | 422/67 |
| 2008/0208481 A1* | 8/2008 | Nakano et al. | 702/19 |
| 2008/0240988 A1* | 10/2008 | Wakamiya et al. | 422/68.1 |
| 2009/0117620 A1* | 5/2009 | Fritchie et al. | 435/91.1 |
| 2014/0250339 A1* | 9/2014 | Ishii | 714/57 |

FOREIGN PATENT DOCUMENTS

| | | |
|---|---|---|
| JP | 10-339732 | 12/1998 |
| JP | 2008-058129 | 3/2008 |

* cited by examiner

FIG.3

| ANALYSIS ID | SAMPLE No. | ANALYSIS ITEM | CELL No. | 1 | ... | 6 | 7 | 8 | 9 | ... | 21 |
|---|---|---|---|---|---|---|---|---|---|---|---|
| NOR210001 | N006242 | FE | 352 | S PIPETTING P1 | | R1 PIPETTING Pos.1-2 P2 | | R1M IX P2 | | | MEASUREMENT |
| NOR210002 | N006243 | FE | 36 | | | S PIPETTING P2 | R1 PIPETTING Pos.1-2 P2 | | R1M IX P2 | | |
| NOR210003 | N006244 | GOT | 126 | | | | | S PIPETTING P2 | R1 PIPETTING Pos.2-7 | | |
| NOR210004 | N006245 | FE | 216 | | | | | | | | |
| CAL110121 | C123 | FE | 306 | | | | | | | | |
| NOR210005 | N006247 | ALT | 396 | | | | | | | | |
| NOR210006 | N006248 | FE | 80 | | | | | | | | S PIPETTING P1 |
| NOR210007 | N006249 | FE | 170 | | | | | | | | |

FIG.4

| ANALYSIS ID | SAMPLE No. | ANALYSIS ITEM | CELL No. | 1 | ... | 6 | 7 | 8 | 9 | ... | 21 |
|---|---|---|---|---|---|---|---|---|---|---|---|
| NOR210001 | N006242 | FE | 352 | S PIPETTING P1 | | R1 PIPETTING Pos.1-2 | | R1M IX P2 | | | MEASUREMENT |
| NOR210002 | N006243 | FE | 36 | | | | | | R1M IX P2 | | |
| NOR210003 | N006244 | GOT | 126 | | | S PIPETTING P2 | | | R1 PIPETTING Pos. 2-7 | | |
| NOR210004 | N006245 | FE | 216 | | | | | S PIPETTING P2 | R1 PIPETTING | | |
| CAL110121 | C123 | FE | 306 | | | | R1 PIPETTING Pos.1-2 | | | | |
| NOR210005 | N006247 | ALT | 396 | | | | | | | | |
| NOR210006 | N006248 | FE | 80 | | | | | | | | S PIPETTING P1 |
| NOR210007 | N006249 | FE | 170 | | | | | | | | |

REAGENT DETAILED INFORMATION AND CALIBRATION CURVE ATTRIBUTE INFORMATION

| | | LOT NAME | EXPIRATION DATE | CALIBRATION CURVE | CALIBRATION ANALYSIS ID |
|---|---|---|---|---|---|
| SAMPLE | N006242 R1 | E0801 | 2007/07/30 | 314-A | CAL110121 |
| ITEM | FE | | | | |

FIG.5

| ANALYSIS ID | SAMPLE No. | ANALYSIS ITEM | CELL No. | 1 | ... | 6 | 7 | 8 | 9 | ... | 21 |
|---|---|---|---|---|---|---|---|---|---|---|---|
| NOR210001 | N006242 | FE | 352 | S PIPETTING P1 | | R1 PIPETTING Pos.1-2 | | R1M IX P2 | | | MEASUREMENT |
| NOR210002 | N006243 | FE | 36 | | | S PIPETTING P2 | R1 PIPETTING Pos.1-2 | | R1M IX P2 | | |
| NOR210003 | N006244 | GOT | 126 | | | | | S PIPETTING P2 | R1 PIPETTING Pos.2-7 | | |
| NOR210004 | N006245 | FE | 216 | | | | | | | | |
| CAL110121 | C123 | FE | 306 | | | | | | | | |
| NOR210005 | N006247 | ALT | 396 | | | | | | | | |
| NOR210006 | N006248 | FE | 80 | | | | | | | | S PIPETTING P1 |
| NOR210007 | N006249 | FE | 170 | | | | | | | | |

ALARM (PHOTOMETER IS ABNORMAL)! ~501

FIG.6

| DATE AND TIME OF S PIPETTING | CELL No. | ANALYSIS ID | SAMPLE No. | ANALYSIS ITEM | SAMPLE CLASSIFICATION |
|---|---|---|---|---|---|
| 2004/03/19 160100 | 36 | NOR210002 | N006243 | FE | SERUM |
| | | ALARM (PHOTOMETER IS ABNORMAL)! — 601 | | | |
| 2004/03/19 160056 | 352 | NOR210001 | N006242 | FE | SERUM |
| 2004/03/19 160053 | 262 | NOR200085 | N006241 | FE | SERUM |
| 2004/03/19 160049 | 172 | NOR200084 | N006240 | FE | SERUM |
| 2004/03/19 160046 | 82 | NOR200083 | N006239 | FE | SERUM |
| 2004/03/19 160042 | 398 | NOR200082 | N006238 | FE | SERUM |
| 2004/03/19 160038 | 308 | NOR200081 | N006237 | FE | SERUM |
| 2004/03/19 160015 | 218 | NOR200080 | N006236 | FE | SERUM |

FIG.8

| No. | ALARM NAME | INFLUENCE RANGE | SEVERITY | NECESSITY OF REINSPECTION |
|---|---|---|---|---|
| 1 | ABNORMAL PHOTOMETER | ALL FIVE ANALYSES BEFORE THE OCCURRENCE TIMING | HIGH | NECESSARY |
| 2 | SAMPLE JAMMED | THREE ANALYSES INCLUDING SAMPLING IN WHICH THE ALARM HAS OCCURRED HOWEVER, THE INFLUENCE RANGE IS LIMITED TO THE SAME SAMPLE | HIGH | NECESSARY |

| ANALYSIS ID | SAMPLE No. | ANALYSIS ITEM | ALARM | CELL No. | 1 | ... | 6 | 7 | 8 | 9 | ... | 21 |
|---|---|---|---|---|---|---|---|---|---|---|---|---|
| NOR21000 1 | N006242 | FE | | 352 | S PIPETTING P1 | | R1 PIPETTING Pos.1-2 | | R1M IX P2 | R1M IX P2 | | MEASUREMENT |
| NOR21000 2 | N006243 | FE | +S! | 36 | | | S PIPETTING P2 | R1 PIPETTING Pos.1-2 | | | | |
| NOR21000 3 | N006243 | GOT | S! | 126 | | | | | S PIPETTING P2 | | | |
| NOR21000 4 | N006243 | FE | | 216 | | | | | | | | |

1001 ALARM (SAMPLE HAS JAMMED)!

AUTOMATIC ANALYZER

BACKGROUND OF THE INVENTION

1. Field of the Invention

The present invention relates to an automatic analyzer for performing biochemical analysis and immunological analysis for blood and the like. The invention more particularly relates to an automatic analyzer which has means for recording information about the operation of analysis equipment constituting an automatic analyzer, information about a situation in which expendable supplies including a reagent are being used, and information about the relation with various kinds of management data and calculation data used in an analysis process, wherein the data (information) stored in the means is displayed in such a way as to be capable of showing the correctness of an analysis process and capable of investigating a cause of an abnormal state. Moreover, the present invention concerns a function of automatically judging whether or not it is necessary to perform reinspection, and of automatically executing the reinspection when it is judged to be executed.

2. Description of the Related Art

An automatic analyzer analyzes a sample such as blood and outputs results of analysis thereof. In such a case, it has been requested to store and present data (information) indicating the validity of the results obtained by the analysis. Information requested for the above purpose includes information about reagent used, calibration curve management information, quality control information, and apparatus maintenance information.

An automatic analyzer performs calibration if necessary so that a calibration curve is determined to calculate the result. The calibration curve is required for each analysis item and for each reagent used. For example, JP-A-10-339732 discloses that various conditions including the remaining amount of reagent, the expiration date of reagent, and the process after a stopper is opened are judged, and an automatic analyzer guides calibration to be executed based on the result of the judgment.

In consideration of the workflow efficiency of a laboratory and the reduction in consumption of expensive reagent, it has recently been possible to utilize the result of another calibration as it is under certain conditions.

On the other hand, when an alarm warning indicative of an abnormal state is output from an automatic analyzer or the quality control carried out by a user warns the user of an abnormal state of the automatic analyzer, the user must quickly investigate the cause of the abnormal state and take appropriate measures.

For a case where the result of analysis is abnormal, for example, JP-A-2008-58129 discloses that selected pieces of information are displayed as information about the analysis and inspection in question on the same screen on an analysis and inspection basis with a sample number or an ID number used as key information, thereby allowing the user to investigate the cause. In this case, the selected pieces of information used include one or more of information selected from among pieces of information including a sample number, ID number information, analysis condition information of the analysis and inspection, reagent pipetting order information, stirring order information, information about a number of a used reaction container, use history report information of the reaction container, reaction process absorbance information, reagent information about used reagent, calibration information, and alarm information.

If the user is warned of an abnormal state of the automatic analyzer, the user stops usual operation and calls a serviceman. The serviceman investigates the operation condition and the maintenance condition of the automatic analyzer, estimates the cause of the abnormal state, and takes measures properly. As occasion requires, the serviceman contacts the manufacturer of the automatic analyzer, extracts data left in the automatic analyzer, and requests the manufacturer to analyze the data.

SUMMARY OF THE INVENTION

Recently, in order that the number of analysis items per unit time is increased for high throughput, various kinds of equipment are configured to operate at high speed. In addition, scheduling of the automatic analyzer is devised so that one automatic analyzer can analyze and inspect various kinds of analysis items. Therefore, it is impossible to follow or estimate the operation of the automatic analyzer based on visual inspection. Thus, the analysis process is regarded as a black box.

To ensure the correctness of an analysis process, it is necessary to acquire information about date, state, and a sample that correspond to conditions when a calibration curve used to calculate the concentration of an analysis item is executed. However, because there are a variety of methods for leaving the result of calibration, detailed information about the analysis and inspection, which have been performed to derive the calibration curve, is not necessarily left.

Moreover, it is not possible to identify the result on quality control for ensuring the accuracy of the analysis and inspection that have been performed to derive the calibration curve.

If the user is warned of an abnormal state of the automatic analyzer, it is difficult for the user to keep the current situation of the automatic analyzer unchanged until the serviceman arrives. The operation condition of the automatic analyzer, which is explained by the user, also lacks in sufficiency and correctness. Moreover, to identify the cause of the abnormal state, it is necessary to organize various kinds of processing along a time axis (in other words, in the order of processing performed in the analysis and inspection) by manpower. Thus, it takes much time until appropriate measures are taken.

If an alarm warning of an abnormal state is output from the automatic analyzer or the quality control carried out by the user warns the user of an abnormal state of the automatic analyzer, the user must eliminate the cause of the abnormal state, and thereafter carry out the analysis and inspection again to obtain the result. In this case, there is no way to know a range within which reinspection is required because the analysis and inspection have been influenced by the abnormal state.

The present invention has been made taking the above-described problems into consideration. An object of the present invention is to provide an automatic analyzer that is capable of easily acquiring information used to evaluate the validity and accuracy of the result of analyzing and inspecting a sample.

Another object of the present invention is to provide an automatic analyzer that is capable of easily acquiring information required to investigate causes and reasons when an abnormal state occurs.

Still another object of the present invention is to provide an automatic analyzer that identifies analysis and inspection, which have been influenced by the occurrence of an abnormal state, to judge whether or not it is necessary to perform reinspection, and that automatically performs the required reinspection.

In order to achieve the above objects, according to one aspect of the present invention, there is provided an automatic analyzer for analyzing constituents of a sample, the automatic analyzer comprising: an analyzing unit including analysis equipment including reaction means, pipetting means, and measurement means; and an operation unit including a storage unit, an input unit, and an output unit; wherein the storage unit stores information about operation performed by the analysis equipment for analysis and inspection, information about a condition when maintenance is performed for the automatic analyzer, information about a process of how expendable supplies such as reagent provided for the analysis and inspection are used, and information used to uniquely identify analysis and inspection performed to derive a calibration curve used for calibration of analysis and inspection; and such that the various kinds of information can be presented such that the result of analysis of the sample can be reviewed.

In addition, according to the present invention, the various kinds of information which can be provided include detailed information about the operation of the automatic analyzer, the detailed information being required for the investigation of a cause of an abnormal state.

Moreover, according to the present invention, the automatic analyzer includes: information used to identify an influence range within which the other analyses and inspection are influenced by the occurrence of the abnormal state; and a function of automatically performing reinspection.

According to the present invention, when the validity and accuracy of the result of analysis are evaluated, various kinds of information about the analysis and inspection, which have been accumulated in a storage unit, can be provided as evidence. This enables a user to make a judgment with accuracy, and to ensure the reliability of the result of analysis.

In addition, because detailed information about the operation of the automatic analyzer can be provided with the detailed information organized in time series, a cause of the abnormal state can be promptly investigated. This makes it possible to quickly take measures such as repairing.

Moreover, because an influence range within which the other analyses and inspection are influenced by the occurrence of the abnormal state can be identified, reinspection can be automatically performed. This enables the user to efficiently ensure the reliability of the result of analysis.

BRIEF DESCRIPTION OF THE DRAWINGS

FIG. 3 is a diagram illustrating an example on output of a detailed history report of an analysis process and analyzer operation according to the embodiment of the present invention;

FIG. 4 is a diagram illustrating, as an example, reagent detailed information and calibration curve attribute information according to the embodiment of the present invention;

FIG. 5 is a diagram illustrating an example in which alarm information is displayed in a detailed history report of an analysis process and analyzer operation along a time axis according to the embodiment of the present invention;

FIG. 6 is a diagram illustrating an example in which an alarm about an abnormal photometer is added to an output history report of a sample probe operation according to the embodiment of the present invention;

FIG. 8 is a diagram illustrating an example of influence range information that is output on an issued alarm basis according to the embodiment of the present invention;

FIG. 10 is a diagram illustrating an example in which a range within which an issued alarm exerts an influence on the analysis and inspection is output along a time axis together with an alarm, and the necessity of reinspection according to the embodiment of the present invention.

DESCRIPTION OF THE PREFERRED EMBODIMENTS

An embodiment of the present invention will be described below with reference to the accompanying drawings.

The configuration of an automatic analyzer according to the present invention will be schematically described with reference to FIGS. 1 and 11.

Figure 11:
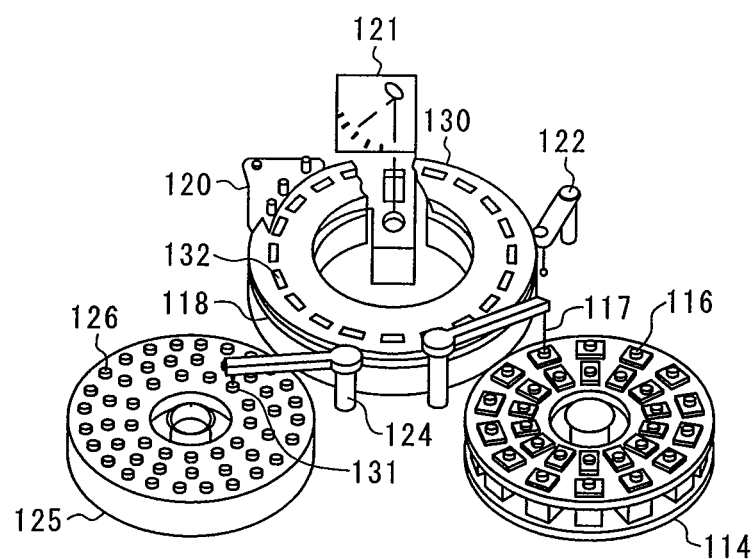
FIG. 11 is a schematic diagram of an automatic analyzer according to the present invention.

FIG. 11 is a schematic diagram of an automatic analyzer according to the present invention. In FIG. 11, a reference numeral 125 represents a sample disk, a reference numeral 114 representing a reagent disk, a reference numeral 130 representing a reaction disk, a reference numeral 118 representing a reaction vessel, a reference numeral 124 representing sample pipetting mechanism, a reference numeral 122 representing a mixer, a reference numeral 121 representing a multiwavelength photometer. A reference numeral 120 represents a rinsing mechanism, a reference numeral 126 representing a sample container, a reference numeral 116 representing a reagent cassette, a reference numeral 132 representing a reaction container, and reference numerals 117 and 131 representing pipetting probes. A plurality of the sample containers are arranged on the sample disk 125.

Next, an operating unit, an analyzing unit, and an interface of the automatic analyzer will be described hereinafter.

Figure 1:
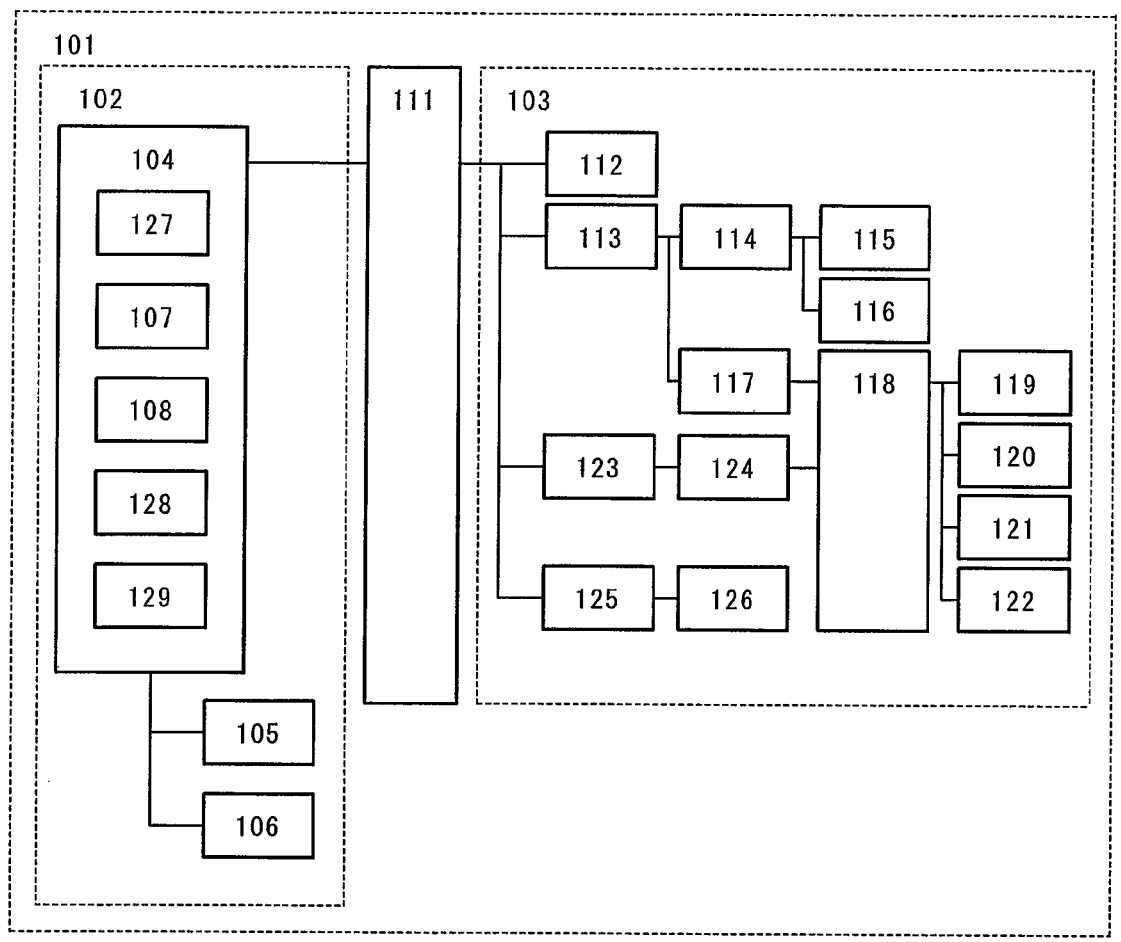
FIG. 1 is a block diagram schematically illustrating the overall configuration of an automatic analyzer according to an embodiment of the present invention.

FIG. 1 is a diagram schematically illustrating the overall configuration of an automatic analyzer that is capable of effectively operating in accordance with the present invention.

An automatic analyzer 101 includes an operation unit 102 and an analyzing unit 103 that is equipped with various kinds of analysis equipment. The operation unit 102 and the analyzing unit 103 exchange information with each other through an interface 111.

The analyzing unit 103 includes an A/D converter 112, a reagent pump 113, a reagent disk 114, a reagent bar-code reader 115, a reagent cassette 116, a reagent pipetting probe 117 that functions as pipetting means, a reaction vessel 118 that functions as reaction means, a cell 119, a rinsing mechanism 120, a multiwavelength photometer 121 that functions as measurement means, a mixer 122, a sample pump 123, a sample pipetting mechanism 124 that functions as pipetting means, a sample disk 125, and a sample container 126.

The automatic analyzer 101 operates by use of each of the above-described elements in the following order: sample pipetting; reagent pipetting; stirring; photometric measurement; and rinsing of a cell. Various kinds of operation performed in the analysis and inspection are known in the art. For example, they are described in JPA-2005-207897.

The operation unit 102 includes a computer 104 for performing the centralized control of the analysis and inspection, an input unit 105 that is connected to the computer 104, and an output unit 106.

The computer 104 for performing the centralized control of the analysis and inspection includes a storage unit 107 and an analysis-ID control unit 108. The storage unit 107 stores information about each piece of equipment constituting the automatic analyzer together with a time stamp. The information stored in this time is operations performed to analyze and inspect a sample, maintenance conditions for the automatic analyzer, and a process of how expendable supplies provided for the analysis and inspection are being used. The analysis-ID control unit 108 gives an ID to analysis and inspection performed to determine a calibration curve as information for identifying analysis and inspection performed to derive the calibration curve. In addition, the computer 104 stores analysis process data 127.

Moreover, every time an alarm occurs, the computer 104 stores information about an influence range, its severity, and whether or not reinspection is required in an influence range information storage unit 128. The computer 104 further includes an influence judgment unit 129 for applying these pieces of information to the alarm that has occurred, and for giving a relevant alarm to the analysis and inspection to perform reinspection judgment.

A generally used keyboard or mouse, a touch panel which operates by touching a CRT, or the like, can be used as the input unit 105. CRT as display means or a printer can be used as an output unit 106. A personal computer that is inexpensive and is high in operability can be used as the operation unit 102.

The various operations in analysis and inspection by the automatic analyzer 101 are performed by the plurality of elements as described above, and further they need to be properly operated. Accordingly, an operator inputs proper control parameters into the operation unit 102.

Essential parts of the present invention will be described as below.

First, an example will be described in which detailed information about the operation of the automatic analyzer is stored in the storage unit 107 on an analysis item basis.

When the automatic analyzer shown in FIG. 1 starts the analysis and inspection of a certain analysis item of a certain sample, first, an analysis ID is given by the analysis-ID control unit 108. The analysis ID is then recorded to the storage unit 107 as key information together with identification information of the sample to be analyzed and inspected, and other data required for the analysis and inspection.

After that, every time each piece of equipment operates, its operation record is additionally stored to the storage unit 107. For example, data recorded when sample pipetting is performed includes "execution date and time", and "the number of a cell used for pipetting". The operation record is stored in chronological order in association with the analysis ID and the analysis item.

Data written when reagent is pipetted includes, for example, "execution date and time", and "a position at which the reagent used for pipetting is located on a reagent disk". As is the case with the sample pipetting, the data is stored in chronological order in association with the above-described analysis ID. However, because reagent is used as an expendable supply, "remaining amount of reagent" is recorded to the storage unit 107 together with "date and time used".

Besides, also for information irregularly created during the analysis and inspection (for example, an abnormal-state notification alarm), "the date and time of occurrence" and "alarm classification" are recorded in the storage unit 107 together with key information of an analysis ID.

Next, analysis process data which is detailed information about the result of analysis performed on an analysis item basis will be described.

Analysis process data 127 is the result of analysis of an analysis item requested for a certain sample and is stored in the computer 104. Using, as keys, identification information including the type and number of a sample that is a target to be analyzed and inspected and an analysis item, the analysis process data 127 includes the analysis ID given by the analysis-ID control unit 108, the result of analysis, detailed information about reagent used, and absorbance data of each wavelength measured by the multiwavelength photometer 121.

The detailed information about reagent used includes a reagent position, a lot name, expiration date, a calibration curve, and an analysis ID used when a calibration curve is determined. Based on the analysis ID used when the calibration curve is determined, actual analysis process data and detailed information about the operation of the automatic analyzer can be recursively traced.

Incidentally, an operator requests the automatic analyzer 101 to analyze and inspect a certain sample for a plurality of analysis items. The automatic analyzer 101 starts the analysis and inspection of one or more samples for one or more analysis items after scheduling is performed in consideration of a plan to use each piece of equipment, wait time it takes to wait for the reaction of reagent, and the like, so that wait time it takes to wait for the result becomes shortest. The result of analysis is not necessarily output in the order requested by the operator.

The analysis process data 127 can be checked in the output unit 106. However because the analysis process data 127 is generated in a general-purpose format, the analysis process data 127 can be written to an external medium as an electronic file so that it can be read on other computers.

Figure 2:
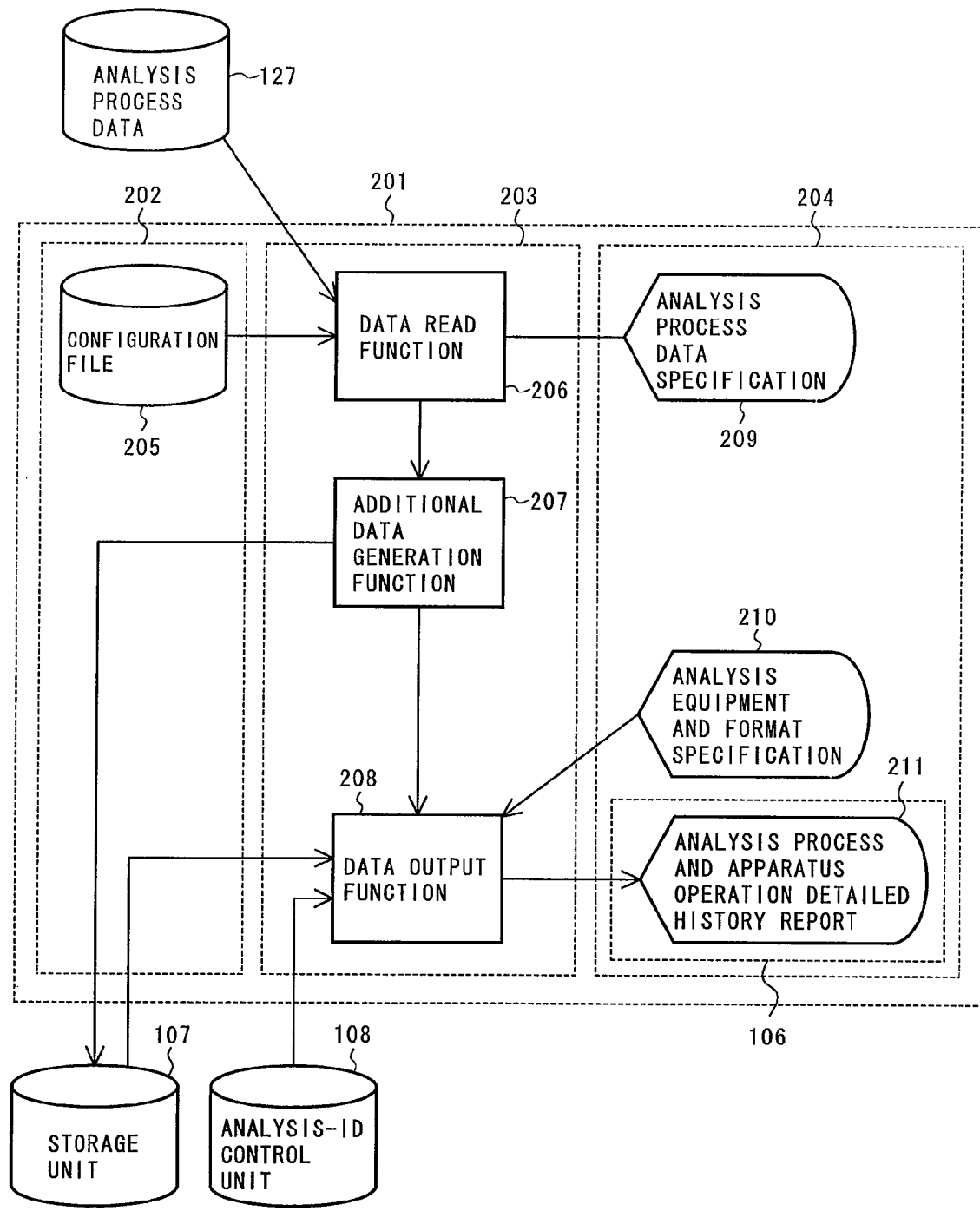
FIG. 2 is a diagram illustrating the overall organization function of a stored data output unit according to the embodiment of the present invention.

FIG. 2 is a system chart illustrating as an example the overall configuration of the automatic analyzer that can embody the present invention, and illustrating how the analysis process data 127, data stored in the storage unit 107, and data stored in the analysis-ID control unit 108, are output to the output unit 106.

A stored-data output unit 201 illustrated in this system chart includes a storage unit 202, a control unit 203, and an input/output unit 204. When a user executes analysis process data specification 209 from the input/output unit 204, a data read function 206 reads a configuration file 205, and then acquires a file format of the specified analysis process data 127. After that, the data read function 206 executes read processing suitable for the file format to acquire the analysis process data 127 in a memory of the data read function 206.

On the basis of the analysis process data 127 acquired in the memory, an additional data generation function 207 generates some pieces of data according to a generation rule. For example, because an operation history report of analysis equipment which is called a sample probe for performing sample pipetting is not included in the analysis process data 127, the operation history report is generated by logically estimating, on the basis of a cell number included in the analysis process data 127, the time at which the sample pipetting has been performed.

The time at which the sample pipetting has been performed can be estimated on the basis of the fact that the operation of the automatic analyzer 101 is executed in the order of sample pipetting, reagent pipetting, stirring, photometric measurement, and rinsing of a cell, and on the basis of an assignment rule of a cell number used when the automatic analyzer 101 schedules analysis and inspection. The generated data is stored in the storage unit 107 shown in FIG. 1.

A data output function 208 converts data stored in the storage unit 107 into data in a format suitable for a purpose, and then displays the data on the output unit 106 as an analysis process and a detailed history report of analyzer operation 211. In this case, a display method suitable for the use of the user can be selected by use of analysis equipment and format specification 210.

A specific example relating to data output will be described as below.

A display example in which evidence used for checking the validity and accuracy of the result of analysis is provided will be described with reference to FIGS. 3 and 4.

FIG. 3 is a diagram illustrating an example of the analysis process and a detailed history report of analyzer operation 211 that are output to the output unit 106 shown in FIG. 1. The analysis process data 127 and each piece of data registered in the storage unit 107 are output along the same time axis in the whole data display area 301 both in the order of samples subjected to the analysis and inspection and in the order of analysis items on which the analysis and inspection have been performed.

In a table header 302 shown in the total data display area 301, each of numbers excluding "Analysis ID", "Sample No.", "Analysis item", and "Cell No." indicates a time zone (for example, a cycle) in which each operation (for example, sample pipetting or reagent pipetting) has been performed. Each analysis process and information about equipment used and expendable supplies used (for example, a reagent) are displayed in each column at the same time.

Thus, from the viewpoint of the analysis process, output information displayed on a CRT of the output unit 106 is displayed in a time-series manner, and at the same time, the output information is displayed in the order of samples that have been subjected to the analysis and inspection. The various kinds of information, which are displayed in such a manner that these pieces of information can be identified at a glance, serve as evidence for evaluation of the validity and accuracy of the result of analysis. On the basis of the provided evidence of the various kinds of information, the user can quickly make a judgment as to whether or not the evaluation of the result of analysis is accurate. This enables the user to ensure the reliability of the result of analysis.

FIG. 4 is a diagram illustrating an example of reagent detailed information shown in FIG. 3. Double-clicking a reagent pipetting display point 401 causes information to be extracted from the data registered in the storage unit 107. The extracted information includes reagent used, calibration curve information used to calculate the concentration of an analysis item, and detailed information about the analysis and inspection performed to derive the calibration curve. The extracted information is output as analysis details 402.

On the basis of information obtained from the analysis details 402, an analysis process can be traced, and reagent used for the analysis and inspection as an expendable supply can be identified. In addition, by concurrently displaying calibration curve information used to calculate the concentration of an analysis item, and detailed information about the analysis and inspection performed to derive the calibration curve, it is possible to provide evidence that the analysis process has been executed under proper management.

Incidentally, because the calibration analysis ID 403 is linked to the analysis ID 404, reviewing of the details of the analysis and inspection makes it possible to recursively check the validity of the derivation of the calibration curve.

Figure 7:
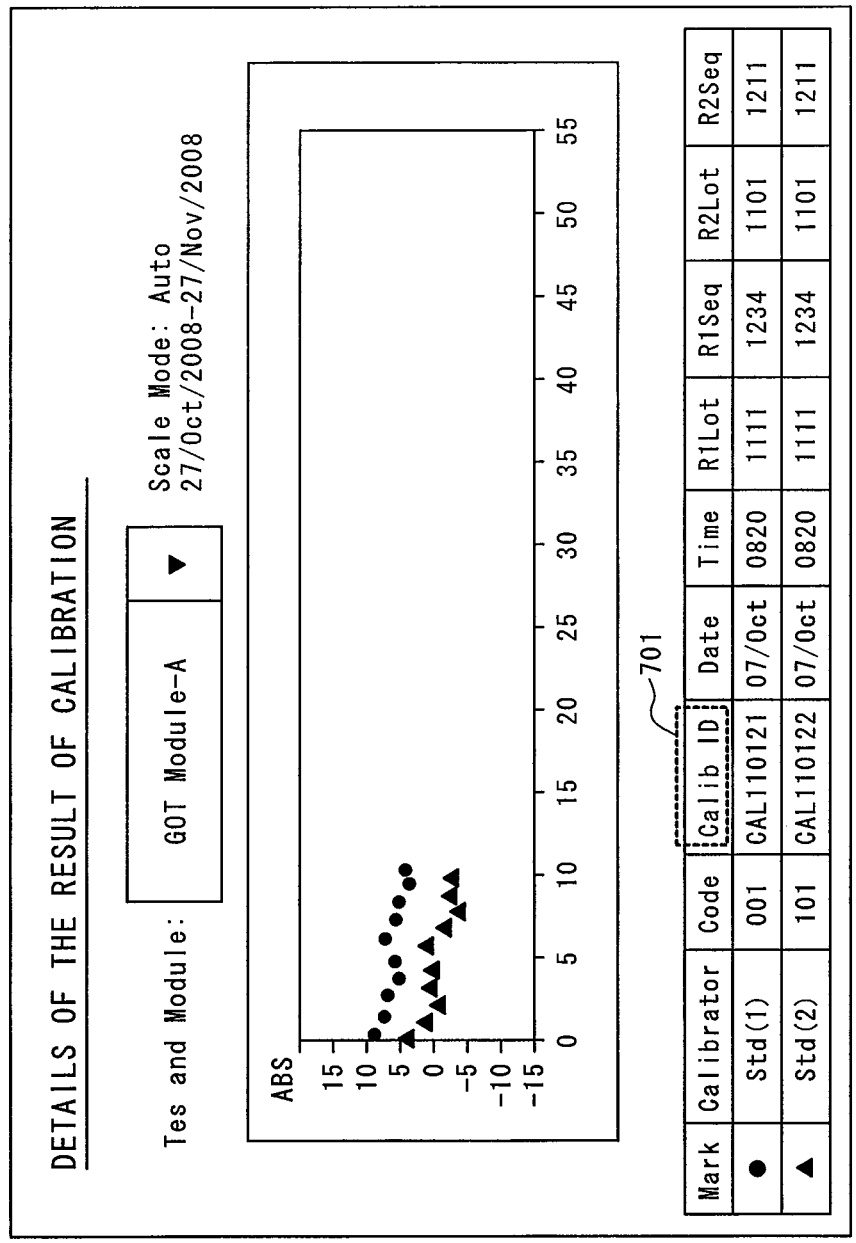
FIG. 7 is a diagram illustrating an example in which details of the result of calibration are output according to the embodiment of the present invention.

FIG. 7 is a diagram illustrating, as an example, details of the result of calibration that are output to the output unit 106. Because the calibration analysis ID 701 is included in displayed information, detailed information about the analysis process, from which the calibration curve has been derived, can be checked by making a search by use of the calibration analysis ID as a key.

As a result of the above processing, the process of the analysis and inspection is shown in order along a time axis together with the detailed information about the operation of the automatic analyzer. This makes it possible to easily check whether or not the sample has been analyzed and inspected according to specified steps by use of properly managed data.

Next, a display example in which the validity of the result of analysis can be checked in conjunction with alarm information will be described with reference to FIG. 5.

In the display example shown in FIG. 3, if an abnormal-state notification alarm is included in a time period displayed in the total data display area 301, the alarm information 501 shown in FIG. 5 is displayed. By directly displaying the alarm information 501 in the total data display area on the basis of "date and time of occurrence", the result of analysis can be shown in such a manner that analyses before and after the occurrence of the abnormal state are clearly discriminated from one another.

Therefore, a user can know in detail the analysis and inspection performed during the time zone associated with the issued alarm, and can also specifically know processing performed in the analysis and inspection in question. This helps the user pay attention not only to the analysis and inspection after the occurrence of the alarm, but also to the analysis and inspection immediately before the occurrence of the alarm. This makes it possible to ensure the reliability of the result.

Next, how to identify and display a range within which analysis and inspection are affected by the issued alarm will be described as an example with reference to FIGS. 8 through 10.

FIG. 8 is a diagram illustrating an example of information stored in the influence range information storage unit 128. An influence range 802, severity 803, and necessity of reinspection 804 are stored on an alarm name 801 basis. These pieces of information can be input and stored by the user through the input unit 105.

When an alarm occurs, information about an influence range, its severity, and necessity of reinspection, which are stored in the influence range information storage unit 128, are searched for by using the issued alarm as a key. Then, on the basis of the information obtained, the influence range is identified, a relevant alarm is given, and a judgment is made as to whether or not it is necessary to perform reinspection. An example of the flow of the above processing will be described with reference to FIG. 9.

First, in step 901, information corresponding to the key is searched for by using an issued alarm as a key. If the information is not found as a result of the search, the process ends. On the other hand, if the information is found as a result of the search, an analysis and inspection influenced by the alarm is identified in 902. Next, in 903, a relevant alarm is given according to the severity. In 904, a judgment is made as to whether or not it is necessary to perform reinspection. If it is judged that it is necessary to perform reinspection, a request for reinspection is made in 905. After the steps 903 through 905 are executed for all analyses and inspection falling within the influence range, the process ends.

The range within the analysis and inspection affected by the issued alarm is displayed in a form as shown in a display area 1001 or 1002 in FIG. 10. This example is based on the assumption that a sample jammed alarm has occurred in the analysis and inspection 1003. In this case, by using the influence range information 805 shown in FIG. 8, it is judged that the sample pipetting 1002 in the analysis and inspection 1004 will be also influenced. Accordingly, an issued alarm is given to the analysis and inspection 1004.

As a result of the above processing, the user can know the analysis and inspection performed in temporal proximity to or in positional proximity to the issued alarm, and can also know whether or not the analysis and inspection have been affected. This makes it possible to ensure the reliability of the result.

Next, how to automatically judge whether or not it is necessary to perform reinspection, and how to perform required reinspection, will be described as an example with reference to FIGS. 9, 10.

Figure 9:
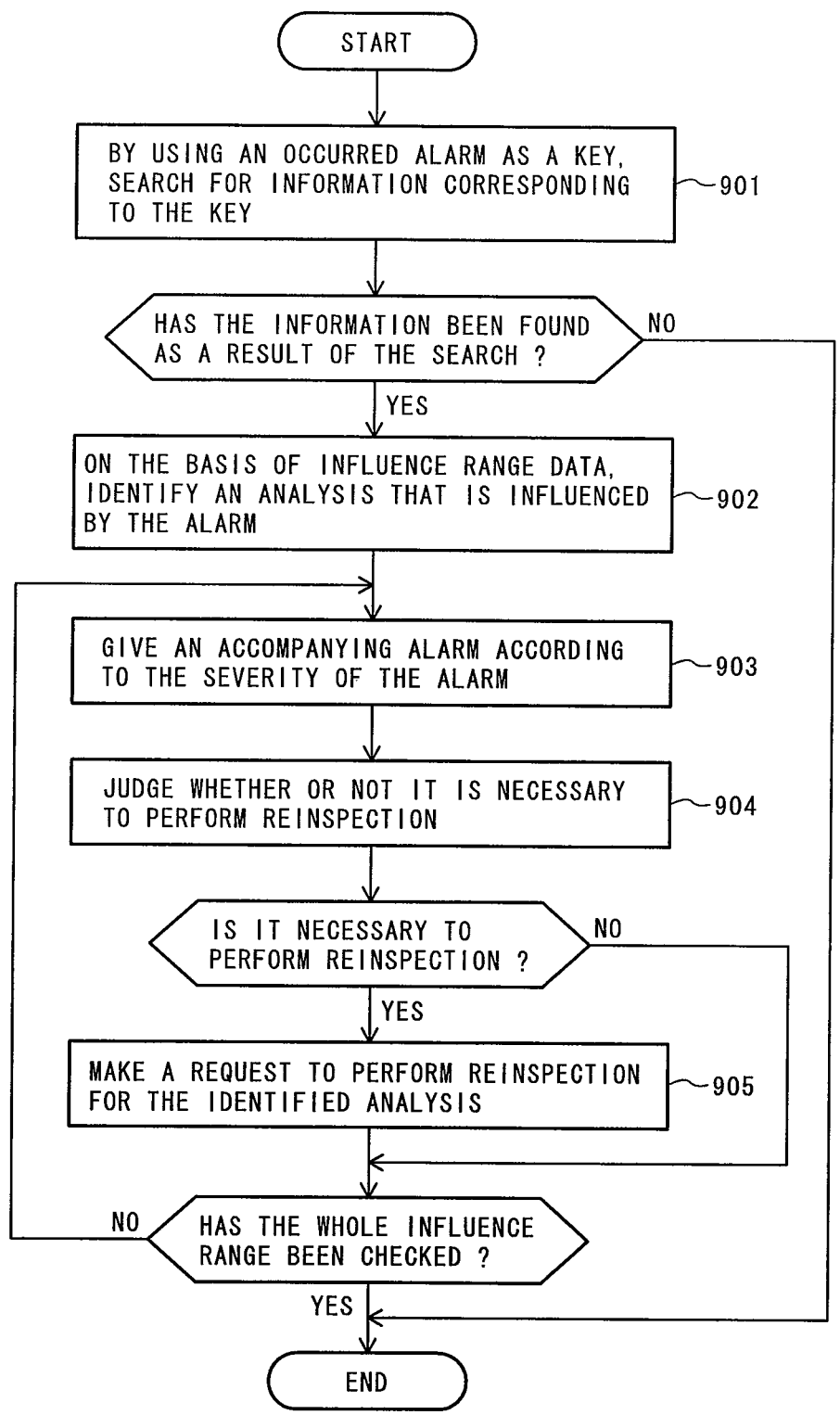
FIG. 9 is a flowchart illustrating an example of the flow in which an influence range is identified, a relevant alarm is given, and a judgment is made as to whether or not it is necessary to perform reinspection according to the embodiment of the present invention.

According to the flowchart shown in FIG. 9, an influence range within which analysis and inspection are affected by an issued alarm is identified, and a judgment is made as to whether or not it is necessary to perform reinspection. The analysis and inspection that are judged to require reinspection are indicated by a display method in which, for example, a background color of a corresponding sample differs from that of an analysis item as shown in a display area 1005 in FIG. 10. The analyzing unit 103 is then automatically instructed to perform reinspection, and consequently, the reinspection is executed.

As a result of the processing described above, reinspection can be effectively performed for the analysis and inspection which may have been influenced by the issued alarm with high possibility.

Next, an example in which detailed information about the operation of the automatic analyzer concerning a plurality of sets of equipment is displayed so that the detailed information can be monitored on the same time axis, will be described with reference to FIG. 6.

FIG. 6 is a diagram illustrating an example of a sample probe operation history report created by specifically extracting data of an operation history report of a sample probe that is equipment for pipetting a sample from the storage unit 107 shown in FIG. 1. A history report of sample pipetting which was performed last is shown in the top line.

When a time period associated with the extracted data includes an abnormal-state notification alarm, the alarm information 601 is displayed. FIG. 6 illustrates an example in which the operation history report of the sample probe is displayed in combination with an abnormal alarm from a photometer. However, other various kinds of probes and reaction cells, and alarms used in an electric system, a mechanical system, and a data processing system, can be displayed in combination.

As a result of the above processing, it becomes possible to view pieces of detailed information about the operation of the automatic analyzer concerning the plurality of sets of analysis equipment in association with one another. Therefore, when an abnormal state of the automatic analyzer occurs, the above-described function contributes to the prompt investigation of the cause of the abnormal state, and prompt measures against the abnormal state. This makes it possible to reduce the non-operating time.

Incidentally, the above embodiment is described on the assumption that mainly a CRT is used for the output unit 106. However, as a matter of course, similar data can also be output to a printer as a report in a similar output format.

With the automatic analyzer configured as described above, an analysis process performed by the automatic analyzer is visualized; and a user can be provided with evidence that data used at the time of the calculation of the concentration in an analysis item is properly managed. This makes it possible to keep the reliability of the analysis and inspection at a high level.

Moreover, the detailed information about the operation of the automatic analyzer, which is required when a cause of an abnormal state is investigated, can be sorted in relation to equipment and a time period. This makes it possible to promptly repair the automatic analyzer. Accordingly, an effect of reducing the non-operating time is exhibited.

Furthermore, based on the causes relevant to an issued abnormal alarm, an influence range within which another analysis and inspection are affected by the alarm can be identified and necessary reinspection is automatically performed. This makes it possible to achieve the effective operation with the high level reliability.

Furthermore, in the embodiments of the invention, the various data can be stored in the storage unit 107 for a predetermined period. After the predetermined period elapsed, the various data stored in the storage unit 107 can be transmitted to a host computer for backup data. The data storage period of the storage unit 107 may be about one week to one month.

What is claimed is:

1. An automatic analyzer comprising:
   an analysis equipment device having sample pipetting means for pipetting samples into reaction containers, reagent pipetting means for pipetting reagents into said reaction containers, and measurement means for analyzing and inspecting components in said samples;
   a controller connected to said analysis equipment device, said sample pipetting means, said reagent pipetting means, and said measurement means;
   a storage unit connected to the controller which is programmed to store in the storage unit:
      information of operation conditions of the analysis equipment device while analyzing and inspecting said samples,
      information concerning expendables used in analyzing and inspecting said samples,
      information of analysis and inspection executed to determine one or more calibration curves used for calibrating the analysis and inspection of said samples, and
      analysis process data of predetermined analysis processes including time information for each of the samples on an analysis item basis; and
   a display section, connected to the controller, for displaying the analysis process data,
   wherein the controller is programmed to:
   control said analysis equipment device according to the predetermined analysis processes required to analyze said samples,
   control said sample pipetting means to pipette samples into reaction containers,
   control reagent pipetting means to pipette reagents into said reaction containers,
   control said measurement means to analyze and inspect components in said samples,
   associate the analysis process data from more than one samples and analysis items based on the time information of each sample from the analysis process data stored in the storage unit, display a time-series arrangement of the analysis process data for more than one of the samples in columns, wherein each column represents a period of time of the predetermined analysis processes required to analyze said samples, and analysis items arranged in rows in the order analyzed by the analysis equipment device in relation to the information of operation conditions of the analysis equipment device while analyzing and inspecting said samples, identify the information concerning expendables used in analyzing and inspecting a particular sample from the information concerning expendables used in analyzing and inspecting said samples stored in the storage unit and identify the information of analysis and inspection executed to determine one or more calibration curves used for calibrating the analysis and inspection of the particular sample from the information of analysis and inspection executed to determine one or more calibration curves used for calibrating the analysis and inspection of said samples stored in the storage unit, display the information concerning expendables used in analyzing and inspecting the particular sample, and the information of analysis and inspection executed to determine one of said calibration curves used for calibrating the analysis and inspection of said particular sample simultaneously on a same display screen in relation to the information of operation conditions of the analysis equipment device while analyzing and inspecting said samples, and detect an abnormal state relating to at least one of the predetermined analysis processes and results thereof, wherein upon detecting an abnormal state by the controller, the controller displays an alarm as a column in the time-series arrangement of the analysis process data immediately after the column representing the time period when the abnormal state relating to the at least one of the predetermined analysis processes and results thereof occurred, wherein said controller is programmed to identify an influence range within which certain ones of the predetermined analysis processes are affected by the alarm, based on causes of said alarm regarding said abnormal state, and wherein said controller is programmed to judge whether it is necessary to perform reinspection for the certain ones of the predetermined analysis processes within the influence range, and automatically performs the required reinspection based on the causes of said alarm for the certain ones of the predetermined analysis processes that are judged to require reinspection.

2. The automatic analyzer according to claim 1, wherein:
said operation conditions include an operational status of said analysis equipment device in the analysis of said samples, and said information concerning expendables includes an indication of a remaining amount of one or more expendable supplies.

3. The automatic analyzer according to claim 1, wherein the controller is programmed to control the display section to display detailed information relating to an investigation of a cause of an abnormal state of one or more of the predetermined analysis processes.

4. The automatic analyzer according to claim 1, wherein the display section includes a display means and a printer.

5. The automatic analyzer according to claim 2, wherein: the display section includes a display means and a printer.

6. The automatic analyzer according to claim 5, wherein said controller is programmed to control the display section to display the analysis process data for more than one of the samples and analysis items simultaneously.

7. The automatic analyzer according to claim 1, wherein the controller is programmed to control the display section to display the analysis and inspection executed to determine one or more calibration curves,
using a unique identifier, which is a displayed analysis item of the analysis items arranged in rows with the analysis process data, for more than one of the samples and analysis items.

8. The automatic analyzer according to claim 1, wherein when said one of said calibration curves displayed on said display section is selectable from among the one or more calibration curves, and
the controller is programmed to control the display section to display said one of said calibration curves along with information specifying at least one of a respective calibrator, information specifying said respective calibrator expiration date, and information specifying a lot number of said respective calibrator.

9. The automatic analyzer according to claim 1, wherein the controller is programmed to control the display section to display the analysis process data for more than one of the samples and analysis items in the time series arrangement in the order the predetermined analysis processes are executed by said automatic analyzer.

10. The automatic analyzer according to claim 1, wherein the controller is programmed to control the display section to display a screen for displaying an influence range regarding whether or not an issued alarm of an analysis result of one of the samples affects the predetermined analysis processes of other samples, and
the controller is programmed to store said influence range information in said storage unit, and said issued alarm is extended to the predetermined analysis processes and analysis results of the other samples on the basis of the influence range.

11. A method of operating an automatic analyzer having a display section, a storage section, analysis equipment device having sample pipetting means for pipetting samples into reaction containers, reagent pipetting means for pipetting reagents into the reaction containers, and measurement means for analyzing components in the samples, and a controller, which is connected to the storage unit, said analysis equipment device, said sample pipetting means, said reagent pipetting means, and said measurement means, and programmed to control said display section, said analysis equipment device, said sample pipetting means, said reagent pipetting means, and said measurement means, the method comprising:

controlling the analysis equipment device according to predetermined analysis processes required to analyze the samples;

storing:
information of operation conditions of the analysis equipment device while analyzing and inspecting said samples,
information concerning expendables used in analyzing and inspecting said samples,
information of analysis and inspection executed to determine one or more calibration curves used for calibrating the analysis and inspection of said samples, and
analysis process data of the predetermined analysis processes including time information for each of the samples on an analysis item basis;

associating the analysis process data from more than one samples and analysis items based on the time information of each sample from the stored analysis process data;

generating a time-series arrangement of the analysis process data for more than one of the samples in columns, wherein each column represents a period of time of the predetermined analysis processes required to analyze said samples, and analysis items in rows in the order analyzed by the analysis equipment device, wherein each row represents an analysis item, in relation to the information of operation conditions of the analysis equipment device while analyzing and inspecting said samples;

displaying said time-series arrangement;

identifying the information concerning expendables used in analyzing and inspecting a particular sample from the stored information concerning expendables used in analyzing and inspecting said samples and identifying the information of analysis and inspection executed to determine one or more calibration curves used for calibrating the analysis and inspection of the particular sample from stored the information of analysis and inspection executed to determine one or more calibration curves used for calibrating the analysis and inspection of said samples;

displaying the information concerning expendables used in analyzing and inspecting the particular sample, and the information of analysis and inspection executed to determine one of said calibration curves used for calibrating the analysis and inspection of said particular sample simultaneously on a same display screen in relation to the information of operation conditions of the analysis equipment device while analyzing and inspecting said samples;

detecting an abnormal state relating to at least one of the predetermined analysis processes and results thereof;

upon detecting an abnormal state, displaying an alarm as a column in the time-series arrangement of the analysis process data immediately after the column representing the time period when the abnormal state relating to the at least one of the predetermined analysis processes and results thereof occurred, identifying an influence range within which certain ones of the predetermined analysis processes are affected by the alarm, based on causes of the alarm regarding the abnormal state, judging whether it is necessary to perform reinspection for the certain ones of the predetermined analysis processes identified within the influence range, and controlling the analysis equipment device to automatically perform the required reinspection based on the causes of the alarm for the certain ones of the predetermined analysis processes that are judged to require reinspection.

12. The method according to claim 11, wherein said operation conditions include an operational status of the analysis equipment device in the analysis of the samples, and said information concerning expendables includes an amount of a remaining amount of one or more expendable supplies.

13. The method according to claim 11, further comprising:

displaying detailed information relating to an investigation of a cause of an abnormal state of one or more of the predetermined analysis processes.

14. The method according to claim 11, wherein the display section includes a display means and a printer.

15. The method according to claim 12, wherein:

the display section includes a display means and a printer.

16. The method according to claim 15, wherein displaying said time-series arrangement includes simultaneously displaying the analysis process data for more than one of the samples and analysis items.

17. The method according to claim 11, wherein the analysis and inspection executed to determine one or more calibration curves are displayed using a unique identifier, which is a displayed analysis item of the analysis items arranged in rows with the analysis process data for more than one of the samples and analysis items.

18. The method according to claim 11, further comprising:

selecting said one of the calibration curves to be displayed; and displaying said one of the calibration curves as graphical information along with information specifying at least one of a respective calibrator, information specifying the respective calibrator expiration date, and information specifying a lot number of the respective calibrator.

* * * * *